US00PP12056P2

(12) United States Plant Patent
Glicenstein

(10) Patent No.: US PP12,056 P2
(45) Date of Patent: Aug. 14, 2001

(54) AZALEA PLANT NAMED 'JEWEL BOX'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/590,627

(22) Filed: Jun. 8, 2000

(51) Int. Cl.[7] ..... A01H 5/00
(52) U.S. Cl. ..... Plt./238
(58) Field of Search ..... Plt./238, 239, 240

(56) References Cited

U.S. PATENT DOCUMENTS

P.P. 3,247 * 8/1972 Henson ..... Plt./239
P.P. 3,355 * 6/1973 Mossholder ..... Plt./238

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Azalea plant named 'Jewel Box', characterized by its dark green, glossy and broad leaves that do not abscise during the cooling and forcing periods; dense, upright and outwardly spreading plant habit; freely branching habit; uniform flowering response; numerous and showy dark pink and white bicolored flowers; hose-in-hose flower form; and excellent postproduction longevity with plants maintaining good flower substance for more than four weeks in an interior environment.

1 Drawing Sheet

BACKGROUND OF THE INVENTION

The present Invention relates to a new and distinct cultivar of Azalea, botanically known as *Rhododenfron hybrida*, an evergreen greenhouse-forcing type Azalea, and hereinafter referred to by the name 'Jewel Box'.

The new Azalea is a product of a planned breeding program conducted by the Inventor in Salinas, Calif. and Alva, Fla. The objective of the breeding program is to create new Azalea varieties having uniform plant habit, profuse and uniform flowering, dark green foliage, good foliage retention during the cooling and forcing periods, resistance to Cylindrocladium, and excellent postproduction longevity.

The new Azalea originated from a cross made by the Inventor in January, 1992, in Salinas, Calif., of the cultivar 'Prize' disclosed in U.S. Plant Pat. No. 3,795, as the female, or seed, parent with the cultivar 'Marian Lee', not patented, as the male, or pollen, parent. The new Azalez was descovered and selected by the Inventor as a flowering plant within the progeny of the stated cross in a controlled environment in Alva, Fla., in June, 1994. The selection of this plant was based on its uniform and dense plant habit, hose-in-hose flower form, dark pink and white bicolored flower color, uniform flowering response, and excellent postproduction longevity.

Asexual reproduction of the new Azalea by terminal cuttings taken in a controlled environment in Alva, Fla., has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Jewel Box'. These characteristics in combination distinguish 'Jewel Box' as a new and distinct cultivar:

1. Dark green, glossy and broad leaves that do not abscise during the cooling and forcing periods.
2. Dense, upright and outwardly spreading plant habit.
3. Freely branching habit.
4. Uniform flowering response.
5. Numerous and showy dark pink and white bicolored flowers.
6. Hose-in-hose flower form.
7. Excellent postproduction longevity with plants maintaining good flower substance for more than four weeks in an interior environment.
8. Very low incidence of infection with Cylindrocladium in inoculated trials.

Plants of the Azalea differ from plants of the female parent, the cultivar 'Prize', in the following characteristics:

1. Plants of the new Azalea have hose-in-hose flowers whereas plants of the cultivar 'Prize' have semi-double to double hose-in-hose flowers.
2. Plants of the new Azalea have dark pink and white bicolored flowers whereas plants of the cultivar 'Prize' have dark rose pink-colored flowers.
3. Plants of the new Azalea have longer postproduction longevity than plants of the cultivar 'Prize'.

Plants of the new Azalea differ from plants of the male parent, the cultivar 'Marian Lee', in the following characteristics:

1. Plants of the new Azalea are denser and more uniform in plant habit than plants of the cultivar 'Marian Lee'.
2. Plants of the new Azalea flower more uniformly than plants of the cultivar 'Marian Lee'.

3. Plants of the new Azalea have hose-in-hose flowers whereas plants of the cultivar 'Marian Lee' have single flowers.
4. Plants of the new Azalea have dark pink and white bicolored flowers whereas plants of the cultivar 'Marian Lee' have red and white bicolored flowers.

Plants of the new Azalea can be compared to the plants of the cultivar 'Parasol', disclosed in U.S. Plant Pat. No. 11,152. However, in side-by-side comparsions conducted by the Inventor in Salinas, Calif., plants of the new Azalea differed from plants of the cultivar 'Parasol' in the following characteristics:

1. Plants of the new Azalea are more freely branching and have a more uniform plant habit than plants of the cultivar 'Parasol'.
2. Plants of the new Azalea flower more profusely and uniformly than plants of the cultivar 'Parasol'.
3. Plants of the new Azalea have dark pink and white bicolored flowers whereas plants of the cultivar 'Parasol' have hot pink and white bicolored flowers.
4. Plants of the new Azalea have longer postproduction longevity than plants of the cultivar 'Parasol'.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the actual colors of the new Azalea.

The photograph at the top of the sheet comprises a side perspective view of a typical plant of 'Jewel Box'.

The photograph at the bottom of the sheet is a close up view of typical flowers of 'Jewel Box'.

DETAILED BOTANICAL DESCRIPTION

The aforementioned and following observations, measurements, values, and comparisons describe multiple plants grown in Salinas, Calfi., in 12.5-cm containers in greenhouses during the spring under commercial production conditions. After flower bud development, plants were cooled at 3 5° C. for four weeks to break flower bud dormancy. Plants were subsequently forced into flower under commercial production conditions in a greenhouse. Plants described were about one year old.

In the following description, color references are made to The Royal Horticultural Society Colour Chart except where general terms of ordinary dictionary significance are used.

Botanical classification:

*Botanical.*—*Rhododendron hybrida* 'Jewel Box'.

*Commercial.*—Evergreen greenhouse-forcing type Azalea.

Parentage:

*Female or seed parent.*—*Rhododendron hybrida* cultivar 'Prize', disclosed in U.S. Plant Pat. No. 3,795.

*Male or pollen parent.*—*Rhododendron hybrida* cultivar 'Marian Lee', not patented.

Propagation:

*Type.*—By terminal vegetative cuttings.

*Time to initiate roots.*— Summer: About 35 days at temperatures of 24° C. Winter: About 42 days at temperatures of 24° C.

*Time to develop roots.*— Summer: About 63 days at temperatures of 24° C. Winter: About 77 days at temperatures of 24° C.

*Root description.*—Vigorous; finely-branched.

Plant description:

*Plant form and growth habit.*—Perennial, evergreen; upright and outwardly spreading plant habit; inverted triangle; moderately vigorous growth habit. Densely foliated. Freely flowering; numerous flowers per plant.

*Branching habit.*—Freely branching; about three or four lateral branches develop after removal of terminal apex.

*Plant height, soil level to top of flowers.*—About 27 cm.

*Plant diameter, area of spread.*—About 38 cm.

*Lateral branch description.*— Length: About 21 cm. Diameter at base: About 7 mm. Texture: Pubescent; fine golden brown hairs. Color: Immature: Close to 146D. Mature: Woody, between 164A and 165B.

Foliage description:

*Arrangement.*—Alternate, single.

*Length.*—About 3.9 cm.

*Width.*—About 2.1 cm.

*Shape.*—Elliptic.

*Apex.*—Cuspidate to mucronate.

*Base.*—Cuneate.

*Margin.*—Entire.

*Texture.*—Leathery, tough; durable; sparsely pubescent.

*Color.*— Young foliage, upper surface: Glossy; darker than 147A. Young foliage, lower surface: 147B. Mature foliage, upper surface: Glossy; darker than 147A. Mature foliage, lower surface: Close to 147B.

*Petiole.*— Length: About 5 mm. Diameter: About 2 mm. Color; Close to 147B to 147C.

Flower description:

*Natural flowering season.*—Spring after sufficient cool period. If forced, plants typically flower about 32 days after a four-week cooling treatment.

*Flower arrangement.*—Flowers arranged singly at terminals with usually about three or four flowers per apex. Flowers face upward and outward. Freely flowering. Not fragrant.

*Flower appearance.*—Hose-in-hose flower form; sepals partially to mostly transformed into petal-like structures. Dark pink and white bicolored petals. Flowers persistent.

*Flower diameter.*—About 6 cm.

*Flower depth.*—About 3.2 cm.

*Postproduction longevity.*—Under interior conditions, plants maintain good flower substance for more than four weeks.

*Flower bud* (*just starting to show petal color*).— Rate of opening: About three to four days depending on temperatures. Length: About 1.75 cm. Diameter: About 6 mm. Shape: Ovoid, elongated. Color: 63B.

*Petals.*— Arrangement: Hose-in-hose flower form; single whorl of five fused petals overlapping; subtended by sepals partially to mostly transformed into petal-like structures. Length: About 4 cm. Width: About 2.6 cm. Shape: Roughly spatulate with rounded or emarginate apex. Margin: Entire; undulating. Texture: Smooth, velvety. Color: When opening, upper surface: 63A to 63B to 64C. When opening, lower surface: 63A to 63B to 64C. Fully opened, upper surface: 63A to 63B; base, white, 155D; iridescent. Fully opened, lower surface: 63A to 63B; base, white, 155D. Spots on upper three petals: On dark pink, spots are dark red, close to 53A; on white, spots are greenish brown.

*Sepals.*— Arrangement: Single whorl of five sepals partially to most transformed into petal-like structures. Shape and size variable. Shape: Mostly lanceolate with mostly acute apex. Marign: Entire. Texture: Sparsely pubescent. Color: 63A to 63B; base, white, 155D; margins, green, close to 144A; dark red spots, close to 53A.

*Peduncles.*— Length: About 6.5 mm. Diameter: About 2 mm. Angle: Upright. Strength: Flexible; strong. Texture: Pubescent. Color: 144A to 144B.

*Reproductive organs.*— Androecium: Stamen quality: Usually about six. Stamen length: About 2.2 cm. Filament color: White. Anther shape: Oblong. Anther size: About 1.5 mm by 1 mm. Anther color; Purple, close to 61A, becoming golden brown with age. Amount of pollen: Moderate. Pollen color: Creamy white. Gynoecium: Pistil quantity: One. Pistil length: About 3.3 cm. Stigma shape: Rounded. Stigma color: 144A to lighter green to white. Style length: About 2.8 mm. Style color: White, 155D. Ovary color: 146A; heavily whiskered.

*Seed.*—Seed production has not been observed.

Disease resistance: In inoculated trials that were conducted in Alva, Fla. during the summers of 1997 and 1999, a very low incidence of infection by Cylindrocladium was observed.

It is claimed:

1. A new and distinct Azalea plant named 'Jewel Box', as illustrated and described.

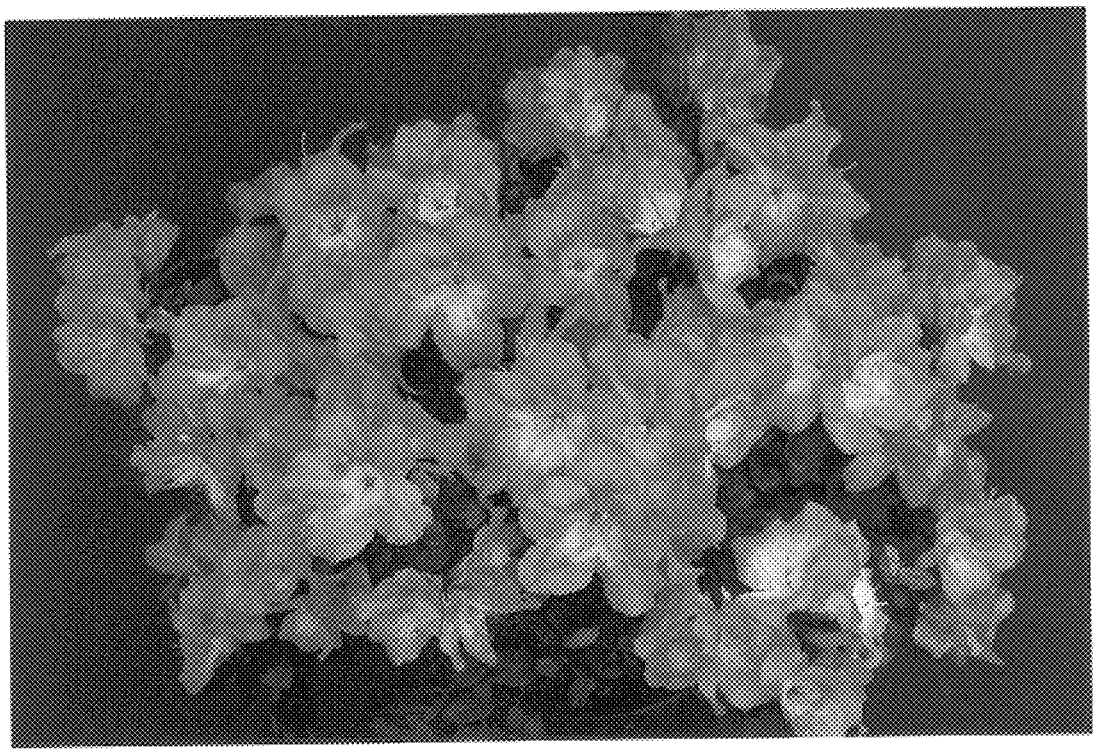
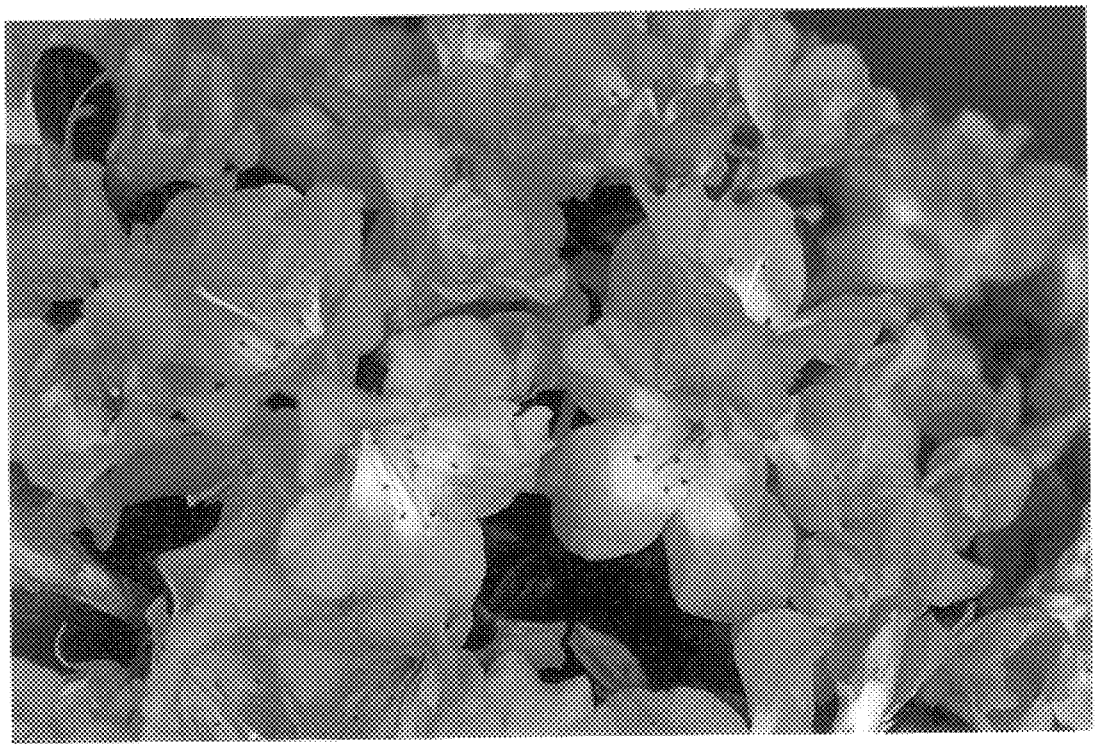

* * * * *